United States Patent
Zhang et al.

(10) Patent No.: US 10,557,947 B1
(45) Date of Patent: Feb. 11, 2020

(54) ANALOG FREQUENCY-DOMAIN MULTIPLEXING FOR TIME-OF-FLIGHT PET DETECTOR FRONTEND ELECTRONICS

(71) Applicant: Siemens Medical Solutions USA, Inc., Malvern, PA (US)

(72) Inventors: Nan Zhang, Knoxville, TN (US); Matthias J. Schmand, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/161,396

(22) Filed: Oct. 16, 2018

(51) Int. Cl.
*G01T 1/208* (2006.01)
*G01T 1/161* (2006.01)
*G01T 1/29* (2006.01)
*A61B 6/03* (2006.01)
*G01R 33/48* (2006.01)
*G01T 1/20* (2006.01)
*G01R 33/563* (2006.01)

(52) U.S. Cl.
CPC .......... *G01T 1/1615* (2013.01); *A61B 6/037* (2013.01); *G01R 33/481* (2013.01); *G01T 1/2985* (2013.01); *G01R 33/5635* (2013.01); *G01T 1/208* (2013.01); *G01T 1/2008* (2013.01)

(58) Field of Classification Search
CPC ....... A61B 6/037; G01T 1/1647; G01T 1/208; G01T 1/2985; G01T 1/2006; G01R 33/481
See application file for complete search history.

(56) References Cited

U.S. PATENT DOCUMENTS

2005/0285541 A1* 12/2005 LeChevalier ............. H01J 3/36
315/169.3
2013/0320218 A1* 12/2013 Woldemichael ...... G01T 1/2985
250/362

OTHER PUBLICATIONS

"Photomultiplier Handbook", Burle Industries, Inc., 1989, pp. 1-179, USA.
S-O Flyckt and Carole Marmonier, "Photomultiplier Tubes Principles & Applications", Photonics, 2002, pp. 1-311, Fiskdale, MA, USA.
"Photomultiplier Tubes Basics & Applications", 3rd ed., Hamamatsu Photonics K. K., 2007, pp. 1-292, Japan.
F. Bauer, et al., "Dynode-Timing Method for PET Block Detectors", IEEE Trans. Nucl. Sci., Feb. 2008, vol. 55, No. 1, pp. 451-456.

* cited by examiner

*Primary Examiner* — David P Porta
*Assistant Examiner* — Fani Boosalis

(57) ABSTRACT

A detector, includes a plurality of photomultiplier tubes each having an anode configured to generate an anode output signal and a frequency domain detector interface including a plurality of frequency domain coupling circuits. Each of the plurality of frequency domain coupling circuits is configured to receive the anode output signal from one of the plurality of photomultiplier tubes and pickoff one of a high-frequency component or a low-frequency component. Each of the plurality of frequency domain coupling circuits is further configured to generate a pass-through signal comprising a first of the high-frequency component or the low-frequency component.

17 Claims, 8 Drawing Sheets

US 10,557,947 B1

ANALOG FREQUENCY-DOMAIN MULTIPLEXING FOR TIME-OF-FLIGHT PET DETECTOR FRONTEND ELECTRONICS

FIELD

Aspects of the present disclosure relate in general to detectors for nuclear imaging, and, more particularly, to frontend processing of signals in nuclear imaging.

BACKGROUND

Nuclear imaging, such as positron emission tomography (PET), generates scintillation pulses based on receipt of positrons at photo detectors during imaging. The scintillation pulses are resolved in respect to time of origin (or time-of-flight (TOF)) and energy. Current systems use operational amplifiers (op-amps) to interface photomultiplier tube (PMT) anode outputs with data acquisition and processing boards. Very-high bandwidth and low noise buffer amplifiers are needed to convert the PMT anode current outputs to a voltage input of the data acquisition and processing boards. Similarly, a very high bandwidth and low noise summing amplifier is needed to sum multiple PMT pulses into energy signals to provide PET timing information through analog timing pickoff methods.

The use of high-bandwidth low-noise summing and buffer amplifiers results in increased cost and reduced reliability in TOF-PET data acquisition electronics. In addition, summing of the PMT anode outputs creates a bottleneck for the analog timing pick-off circuits. A conventional summing combines multiple PMT anode outputs through a high-speed op-amp, making it difficult to meet the high slope-to-noise ratio (NSR) requirements. Conventional systems further branch broadband signals into two paths for positioning and timing. Such branching is inefficient and under optimizes the signal-to-noise ratio (SNR) for positioning and energy and/or the NSR for timing.

SUMMARY

In various embodiments, a detector is disclosed. The detector includes a plurality of photomultiplier tubes each having an anode configured to generate an anode output signal and a frequency domain detector interface including a plurality of frequency domain coupling circuits. Each of the plurality of frequency domain coupling circuits is configured to receive the anode output signal from one of the plurality of photomultiplier tubes and pickoff one of a high-frequency component or a low-frequency component. Each of the plurality of frequency domain coupling circuits is further configured to generate a pass-through signal comprising a first of the high-frequency component or the low-frequency component.

In various embodiments, a detector circuit is disclosed. The detector circuit includes a plurality of photomultiplier tubes each having an anode configured to generate a broadband anode output signal and a frequency domain detector interface including a plurality of diplexing coupling circuits. Each of the plurality of diplexing coupling circuits is configured to receive the broadband anode output signal from one of the plurality of photomultiplier tubes and generate a narrowband low-frequency signal and a narrowband high-frequency signal.

In various embodiments, a detector circuit is disclosed. The detector circuit includes a plurality of photomultiplier tubes each having an anode configured to generate an anode output signal and a frequency domain detector interface including a plurality of coupling circuits. Each of the plurality of coupling circuits is configured to receive the anode output signal from one of the plurality of photomultiplier tubes and generate a low-frequency output signal and a high-frequency output signal. An analog frontend is configured to receive the low-frequency output signal and generate one of a single-ended signal or a differential signal. A summation timing circuit is configured to receive the high-frequency output signal and generate a summed high-frequency signal. A timing pickoff circuit is configured to receive the summed high-frequency signal and generate a timing pickoff signal.

BRIEF DESCRIPTION OF THE DRAWINGS

The following will be apparent from elements of the figures, which are provided for illustrative purposes and are not necessarily drawn to scale.

DETAILED DESCRIPTION

This description of the exemplary embodiments is intended to be read in connection with the accompanying drawings, which are to be considered part of the entire written description.

Various embodiments of the present disclosure address the foregoing challenges associated with PMT output signal conversion by implementing frequency-domain multiplexing (MUX) systems and methods to buffer predetermined components of the PMT anode output signals. In some embodiments, a frequency domain detector interface is configured to pickoff (i.e., remove or filter) one of a high-frequency component or a low-frequency component of each of a plurality of PMT anode output signals and generate a pass-through signal including a second of the high-frequency component or the low-frequency component. In some embodiments, a broadband PMT anode output signal is split into a first narrowband signal corresponding to a high-frequency component of the broadband PMT anode output signal and a second narrowband signal corresponding to a low-frequency component of the broadband PMT anode output signal. The frequency-domain detector interfaces utilize passive, analog circuit components that decrease cost and provide timing improvements to PMT anode output signal acquisition and conversion.

Figure 1:
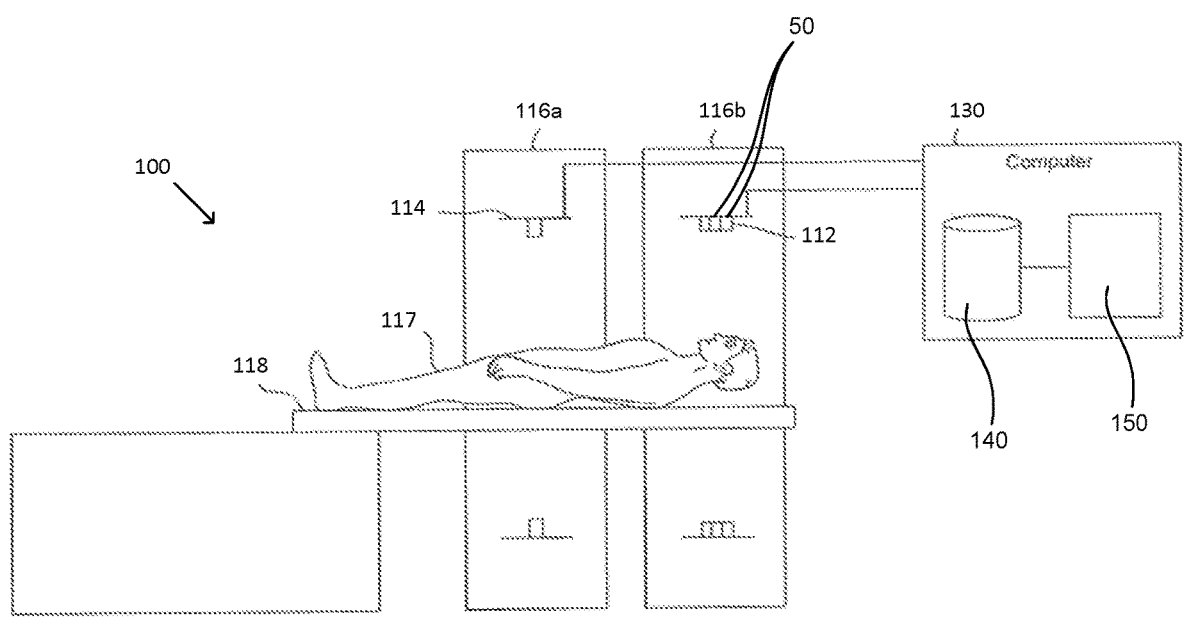
FIG. 1 illustrates a PET imaging system, in accordance with some embodiments.

FIG. 1 illustrates one embodiment of a nuclear imaging detector 100. The nuclear imaging detector 100 includes a scanner for at least a first modality 112 provided in a first gantry 116a. The first modality 112 includes a plurality of detectors 50 configured to detect an annihilation photon, gamma ray, and/or other nuclear imaging event. In various embodiments, the first modality 112 is a PET detector. A patient 117 lies on a movable patient bed 118 that may be movable between a gantry. In some embodiments, the nuclear imaging detector 100 includes a scanner for a second imaging modality 114 provided in a second gantry 116b. The second imaging modality 114 can be any suitable imaging modality, such as, for example, computerized tomography (CT), single-photon emission tomography (SPECT) and/or any other suitable imaging modality.

Scan data from the first modality 112 is stored at one or more computer databases 140 and processed by one or more computer processors 150 of a computer 130. The graphical depiction of computer 130 in FIG. 1 is provided by way of illustration only, and computer 130 may include one or more separate computing devices. The imaging data sets can be provided by the first modality 112 and/or may be provided as a separate data set, such as, for example, from a memory coupled to the computer 130. The computer 130 can include one or more processing electronics for processing a signal received from one of the plurality of detectors 50.

Figure 2:
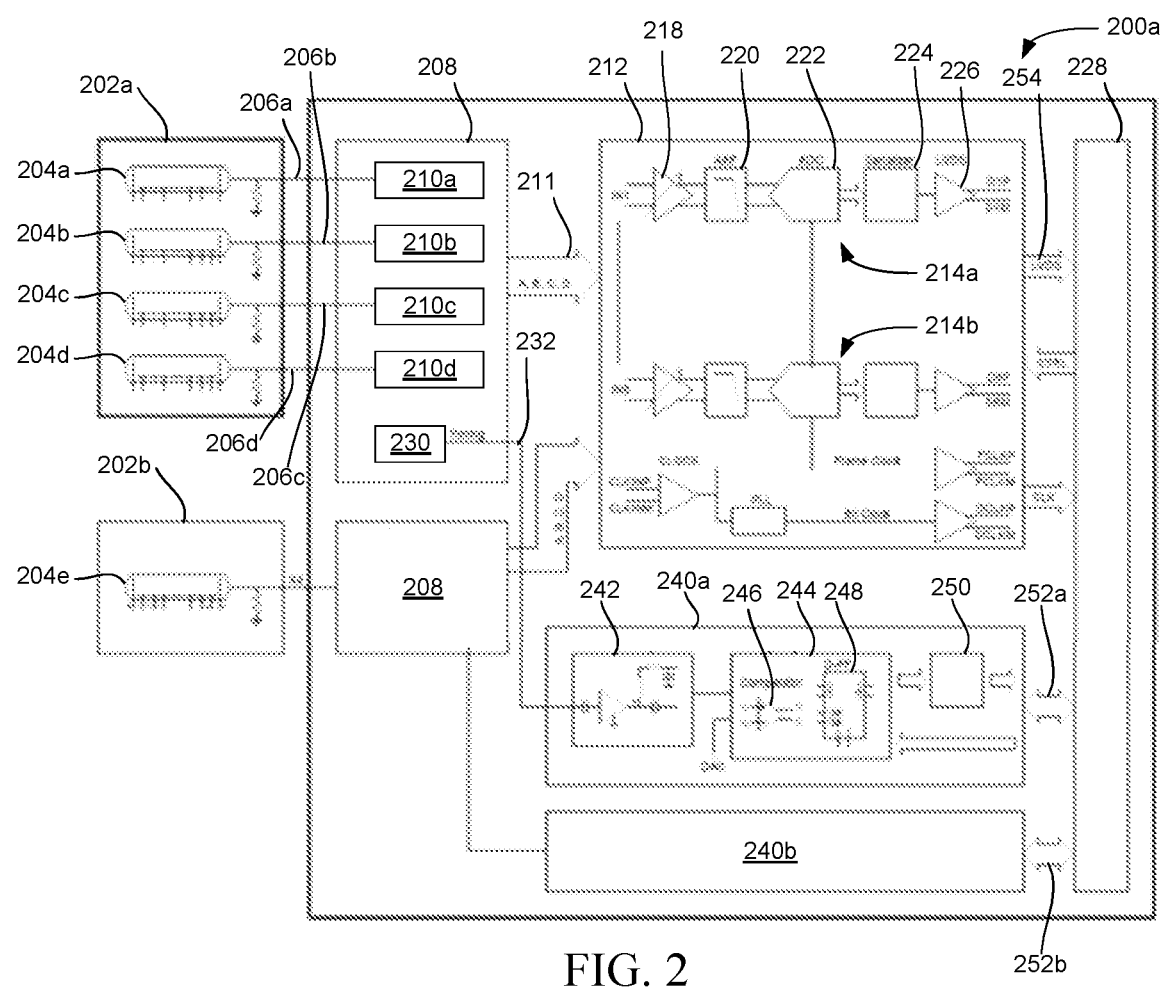
FIG. 2 illustrates a read-out circuit including a frequency domain detector interface, in accordance with some embodiments.

FIG. 2 illustrates a read-out circuit 200a including a plurality of frequency domain detector interfaces 208, in accordance with some embodiments. The read-out circuit 200a includes a plurality of positron emission tomography (PET) detectors 202a, 202b. Each of the PET detectors 202a, 202b includes a plurality of photomultiplier tubes (PMTs) 204a-204d configured to generate an analog anode signal 206a-206d. In the illustrated embodiment, each of the PMTs 204a-204d and the respective analog anode signal 206a-206d output by each of the PMTs 204a-204d of the first PET detector 202a are shown individually, while the PMTs 204e and the anode signals 206e of the second PET detector 202b are shown collectively. Although embodiments are shown with PET detectors 202a, 202b having four PMTs 204a-204d, it will be appreciated that each PET detector 202a, 202b can have any number of PMTs 204a-204d and/or generate any number of PMT anode signals 206a-206d.

In some embodiments, each PMT anode signal 206a-206d of a first PET detector 202a is provided to a first frequency domain detector interface 208. Each frequency domain detector interface 208 includes a plurality of frequency domain coupling circuits 210a-210d configured to pickoff one of a low-frequency component or a high-frequency component of the PMT anode signal 206a-206d and generate a pass-through component 211 for each anode signal 206a-206d. The pass-through component 211 is provided to an analog frontend 212. Each frequency domain detector interface 208 is configured to provide smoothed pass-through component signals 211 to improve energy resolution and event positioning measurement of the analog frontend 212, for example, by enabling low-sampling rates and low-cost digitization analog-to-digital converters (ADCs). Various embodiments of frequency domain detector interfaces 208 are illustrated in FIGS. 3 and 5A-5D and are discussed in greater detail below.

The analog frontend 212 includes a plurality of conversion paths 214a, 214b each configured to convert a pass-through component signal 211 associated with one of the anode signals 206a-206d to a low-voltage differential signal 254. In some embodiments, each of the conversion paths 214a, 214b includes a plurality of integrated circuit elements and/or discrete circuit elements configured to convert the respective pass-through component signal 211 to a low-voltage differential signal 254. For example, in the illustrated embodiment, each conversion path 214a, 214b includes an amplifier 218 configured to receive a pass-through component 211 from a corresponding one of the frequency domain coupling circuits 210a-210d. The amplifier 218 amplifies and passes the pass-through component signal to a filter 220, such as an anti-aliasing filter. The output of the filter 220 is provided to an analog-to-digital converter (ADC) 222, which converts the received analog signal to a digital signal which is provided to a serializer 224. The serializer 224 provides a serialized, digital output to a low-voltage differential signaling circuit 226, which provides the digital energy signal 254 to a controller 228. In some embodiments, the controller 228 uses the low-voltage differential signal 254 generated for each anode signal 206a-206d for energy acquisition. Although embodiments are discussed herein including conversion paths 214a, 214b having specific components, it will be appreciated that one or more circuit elements illustrated in the analog frontend 212 can be combined, for example, within a single integrated circuit (IC) and/or a plurality of ICs. It will further be appreciated that one or more circuit elements can be replaced, omitted, and/or added to each of the conversion paths 214a, 214b.

In some embodiments, each detector interface 208 includes a summation timing circuit 230 configured to generate a summed signal 232. The summation timing circuit 230 receives a selected component of each of the anode signals 206a-206d and generates the summed signal. In some embodiments, the summation timing circuit 230 is configured to receive a high-frequency component of each of the anode signals 206a-206d. In some embodiments, the timing circuit 230 is a passive circuit. Various embodiments of a timing circuit 230 are illustrated in FIGS. 4A-4D and are discussed in greater detail below. Each PMT anode operates as an ideal current source and the high source impedance of the PMT anode prevents the individual anode signals 206a-206d from being back-coupled to each of the other frequency domain coupling circuits 210a-210d.

In some embodiments, the summed single 232 of each frequency domain detector interface 208 is provided to a respective analog timing pickoff circuits 240a, 240b. The analog timing pickoff circuits 240a, 240b are configured to generate timing pickoff signals 252a, 252b, respectively, which are used by the controller 228 for timing (e.g., ToF) acquisition. For example, in the illustrated embodiment, the analog timing pickoff circuit 240a includes a low-noise amplifier 242, a leading edge discriminator circuit 244 including a comparator 246 and a d-type flip-flop 248, and a time-to-digital convertor (TDC) circuit 250. Although specific embodiments of the analog timing pickoff circuits 240a, 240b are illustrated herein, it will be appreciated that any suitable pickoff circuit can be used to generate the timing pickoff signal 252a, 252b (corresponding to the analog timing pickoff circuits 240a, 240b). The timing pickoff signal 252a, 252b is provided to the control circuit 228.

The control circuit 228 can include any suitable circuit or device configured to receive at least the timing pickoff signal 252 and the low-voltage differential signal 254. The control circuit 228 can be configured to store the received signals, process the received signals to generate timing and/or energy information (e.g., scan data), and/or otherwise process the received data. The control circuit 228 can include one or more of a microprocessor, a field-programmable gate-array (FPGA), an application-specific integrated circuit (ASIC), a microcontroller, and/or any other suitable controller and/or combination of controllers.

Figure 3:
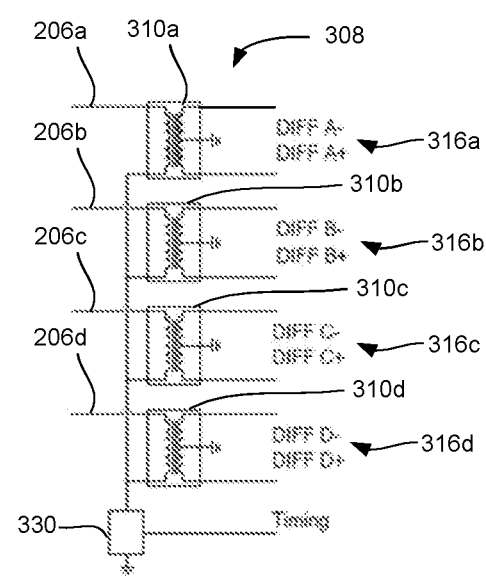
FIG. 3 illustrates a frequency domain detector interface configured for low-frequency pickoff, in accordance with some embodiments.

FIG. 3 illustrates a frequency domain detector interface 308 configured for low-frequency pickoff, in accordance with some embodiments. The frequency domain detector interface 308 is similar to the frequency domain detector interface 208 described above in conjunction with FIG. 2, and similar description is not repeated herein. The frequency domain detector interface 308 includes a plurality of low-frequency coupling circuits 310a-310d each configured to pickoff a low-frequency component of a respective PMT anode signal 206a-206d and pass-through a high-frequency component of the respective anode signal 206a-206d to the analog frontend 212. In some embodiments, each of the low-frequency coupling circuits 310a-310d includes a balanced-to-unbalanced (Balun) transformer configured to pickoff low-frequency components of the PMT anode signals 206a-206d and generate a differential output 316a-316d corresponding to the high-frequency component. The differential outputs 316a-316d are provided as inputs to the analog frontend 212.

Figure 4A:
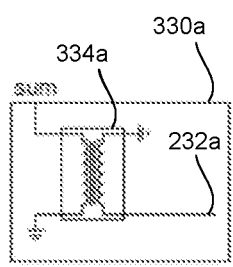
FIG. 4A illustrates a passive transformer-coupled summing circuit having an inverting polarity, in accordance with some embodiments.
Figure 4B:
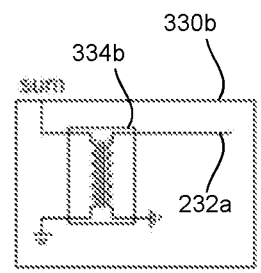
FIG. 4B illustrates a passive transformer-coupled summing circuit having a non-inverting polarity, in accordance with some embodiments.

In some embodiments, the frequency domain detector interface 308 includes a summation timing circuit 330 configured to generate a summed output signal 232 for timing pickoff. FIGS. 4A-4D illustrate various embodiments 330a-330d of the summation timing circuit 330 configured to be integrated with a frequency domain detector interface 208, 308. FIGS. 4A and 4B each illustrate a summation timing circuit 330a, 330b including a radiofrequency (RF) transformer 334a, 334b. FIG. 4A illustrates the RF transformer 334a having a first (inverting) polarity and FIG. 4B illustrates the RF transformer 334b having a second (non-inverting) polarity. An output of each of the RF transformer 334a, 334b provides the summed output signal 232 to one of the analog timing pickoff circuits 240a, 240b.

Figure 4C:
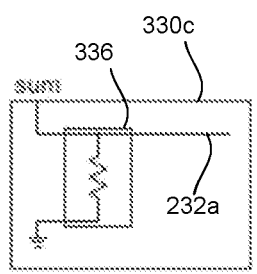
FIG. 4C illustrates a passive resistive-load summing circuit, in accordance with some embodiments.
Figure 4D:
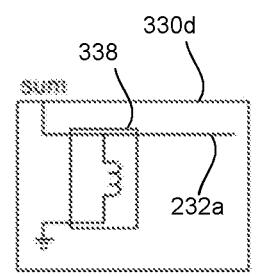
FIG. 4D illustrates a passive inductive-load summing circuit, in accordance with some embodiments.

FIG. 4C illustrates a resistive-load based summation timing circuit 330c, in accordance with some embodiments. A resistive load 336 is configured to passively generate the summed signal 232. FIG. 4D illustrates an inductive-load based summation timing circuit 330d. The inductive-load 338 is configured to pre-emphasize the high-frequency component of the summed signal 232. Although the inductive-load 338 is complimentary to high-frequency pickoff (described in greater detail below), inductive-load based summation timing circuits 330d can be configured for low-frequency timing summation.

Figure 5A:
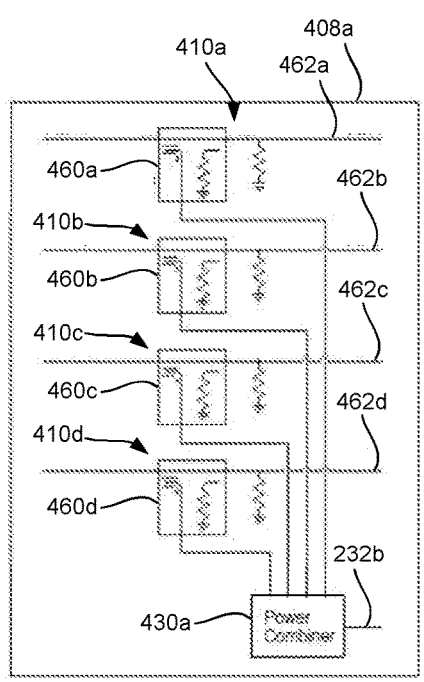
FIG. 5A illustrates a frequency domain detector interface having a plurality of RF directional couplers configured for high-frequency pickoff, in accordance with some embodiments.

FIGS. 5A-5D illustrate various frequency domain detector interfaces 408a-408d configured for high-frequency pickoff, in accordance with some embodiments. The frequency domain detector interfaces 408a-408d are similar to the frequency domain detector interface 208 described in conjunction with FIG. 2, and similar description is not repeated herein. FIG. 5A illustrates a frequency domain detector interface 408a including a plurality of detector circuits 410a-410d each including an RF directional-coupler 460a-460d. Each of the RF directional-couplers 460a-460d are configured to pickoff the high-frequency component of a respective anode signal 206a-206d provided to the respective detector circuit 410a-410d and pass-through the low-frequency component to an analog frontend 212. For example, in some embodiments, the RF directional-couplers 460a-460d each generate a single-ended signal 462a-462d indicative of the low-frequency component of a respective anode signal 206a-206d.

Figure 5B:
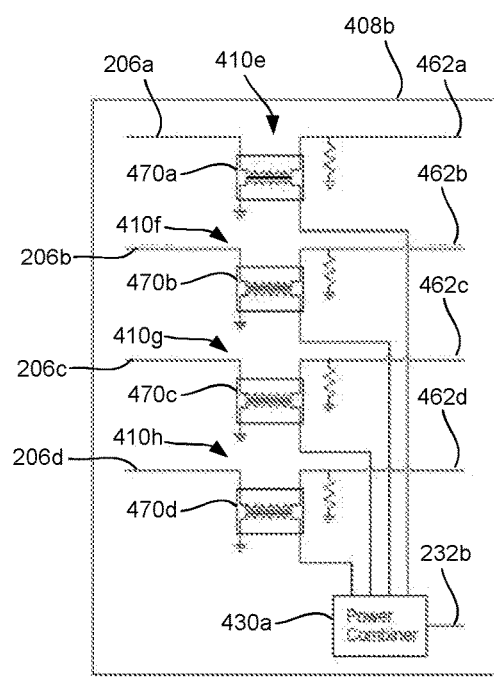
FIG. 5B illustrates a frequency domain detector interface having a plurality of transformers configured for high-frequency pickoff, in accordance with some embodiments.
Figure 5C:
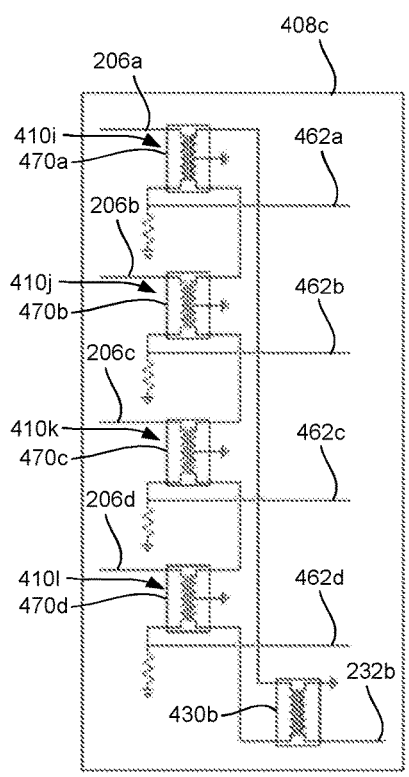
FIG. 5C illustrates a frequency domain detector interface having a plurality of transformers configured for high-frequency pickoff, in accordance with some embodiments.
Figure 5D:
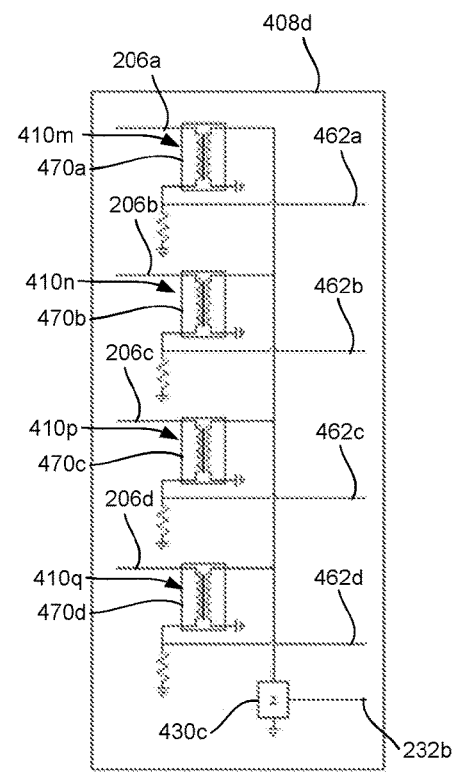
FIG. 5D illustrates a frequency domain detector interface having a plurality of transformers configured for high-frequency pickoff, in accordance with some embodiments.

FIGS. 5B-5D illustrate frequency domain detector interfaces 408b-408d including a plurality of high-frequency coupling circuits 410e-410q including RF transformers 470a-470d. Each of the RF transformers 470a-470d is configured to pickoff a high-frequency component of a respective anode signal 206a-206d and convert the low-frequency component to a single-ended voltage signal 462a-462d. The single-ended voltage signal 462a-462d is provided to the analog frontend 212.

In some embodiments, each of the frequency domain detector interfaces 408a-408d include a summation timing circuit 430a-430c configured to generate a summed signal 232 for timing pickoff. For example, as illustrated in FIGS. 4A and 4B, the summation timing circuit can include a power combiner summation timing circuit 430a. The power combiner summation timing circuit 430a includes an RF power-combiner configured to provide a constant impedance load for input and/or output ports, such as, for example, 50Ω, 75Ω, etc. The power combiner generates the summed output 232 for timing pickoff. As another example, as illustrated in FIG. 4C, the summation timing circuit 430a-430c can include an RF transformer summation timing circuit 430c. The RF summation timing circuit 430c is similar to the RF summation timing circuits 330a-330b described in conjunction with FIGS. 4A-4B, and similar description is not repeated herein.

As yet another example, and as illustrated in FIG. 4D, the summation timing circuit 430 can include a load-based summation timing circuit 430d. The load-based summation timing circuit 430d can include a resistive-load based circuit (such as the resistive load based summation timing circuit described in conjunction with FIG. 4C), an inductive-load based circuit (such as the inductive load-based summation timing circuit described in conjunction with FIG. 4D), and/or any other suitable load-based summation timing circuit. Although specific embodiments of frequency domain detector interfaces 408a-408d are shown having certain summation timing circuits 430a-430d, it will be appreciated that any of the frequency domain detector interfaces 408a-408d can include any of the summation timing circuits 430a-430d illustrated herein.

Figure 6:
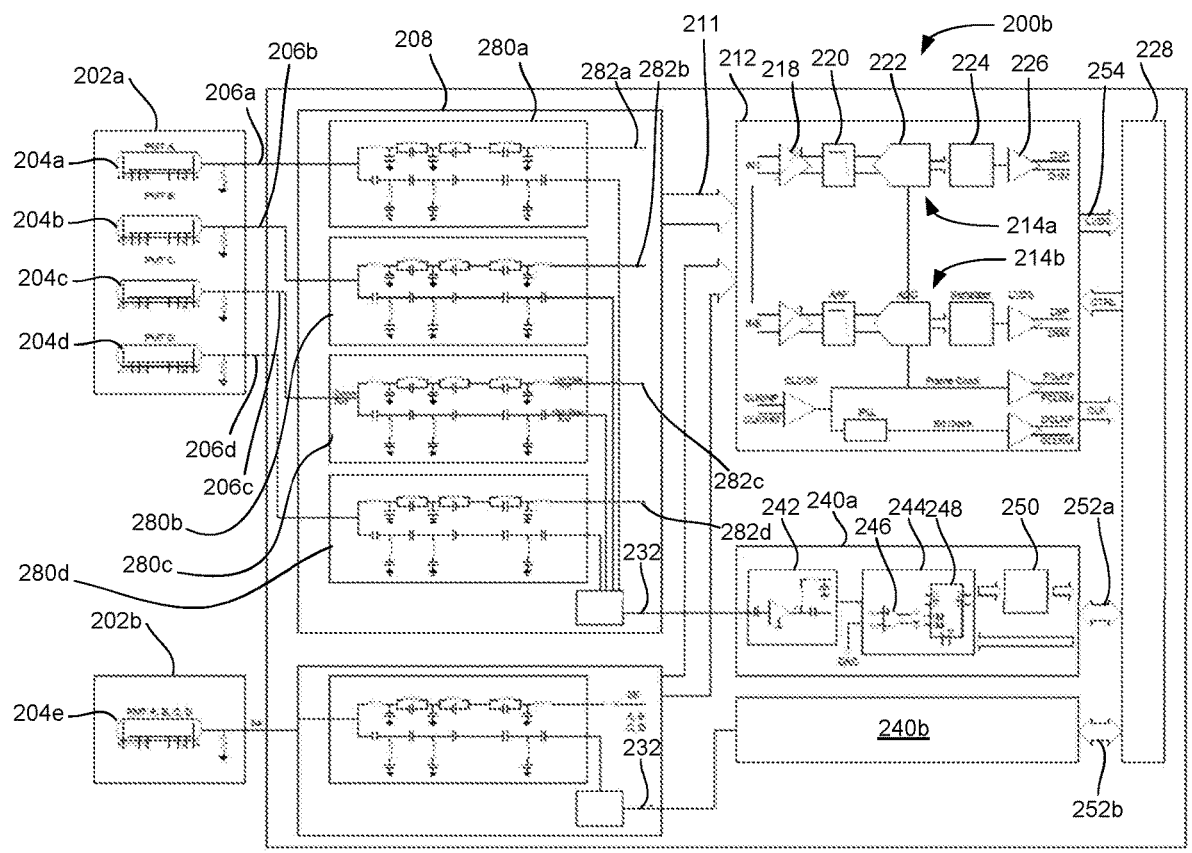
FIG. 6 illustrates a read-out circuit including a frequency domain detector interface having a plurality of split detector circuits, in accordance with some embodiments.

FIG. 6 illustrates a read-out circuit 200b including frequency domain detector interfaces 208a each having a plurality of duplexing coupling circuits 280a-280d, in accordance with some embodiments. The read-out circuit 200b is similar to the read-out circuit 200a discussed above and similar description is not repeated herein. Each duplexing coupling circuit 280a-280d is configured to separate a wideband PMT anode signal 206a-206d into a low-frequency component signal 282a-282d and a high-frequency component signal 284a-284d. In some embodiments, the low-frequency component 282a-282d is provided to the analog frontend 212 and a high-frequency component 284a-284d (see FIG. 7) is provided to a summation timing circuit 230.

Figure 7:
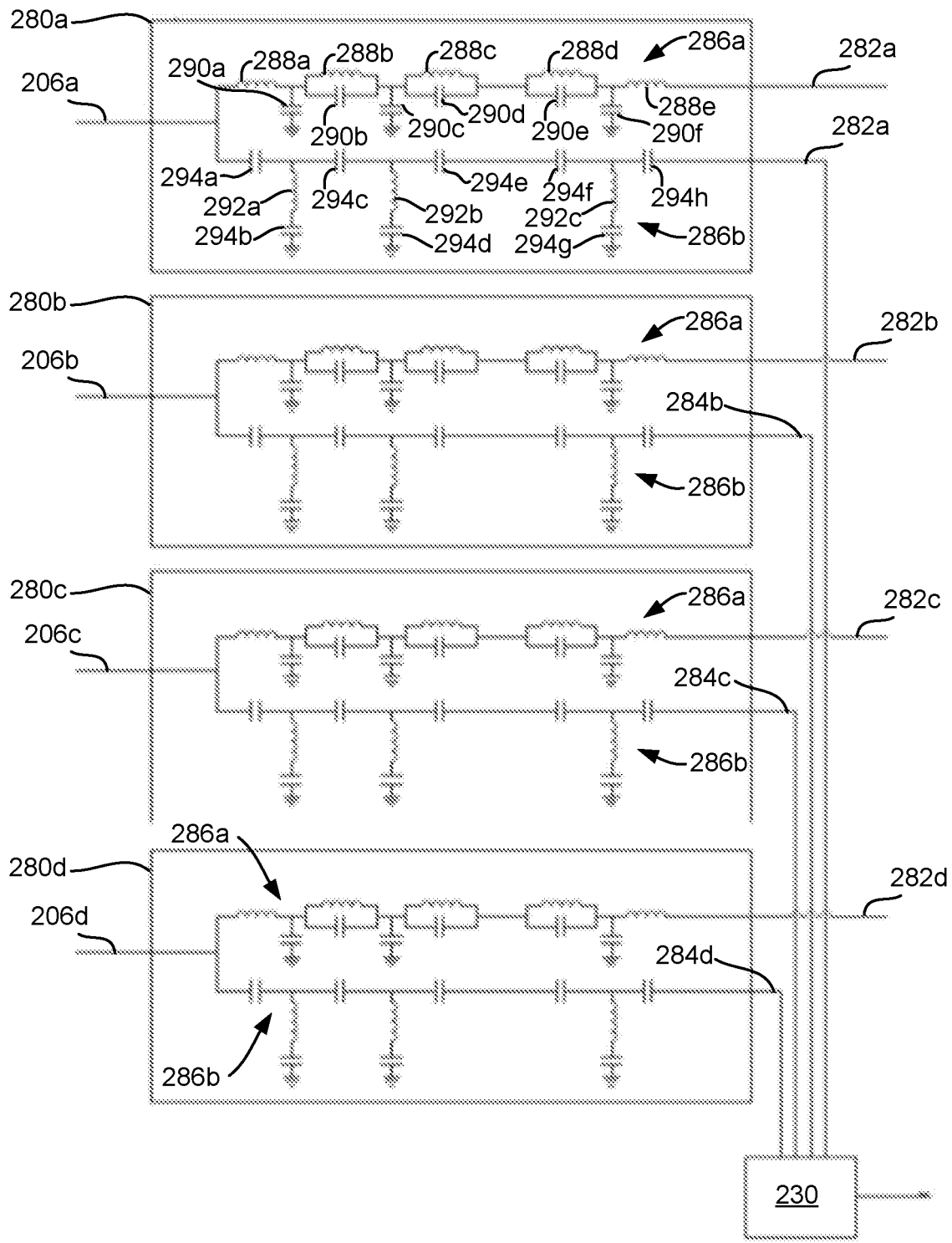
FIG. 7 illustrates the frequency domain detector interface of FIG. 6, in accordance with some embodiments.

As illustrated in FIG. 7, each of the diplexer circuits 280a-280d includes a low-frequency path 286a and a high-frequency path 286b. The low-frequency path 286a includes a plurality of inductive and/or capacitive elements configured to act as a low-pass filter to isolate the low-frequency component of the respective anode signal 206a-206d. For example, in the illustrated embodiment, the low-frequency path 254 includes a plurality of inductive elements 288a-288e and a plurality of capacitive elements 290a-290f configured to provide low-pass filtering to isolate the low-frequency component of the respective anode signal 206a-206d. Similarly, the high-frequency path 286b includes a plurality of inductive elements 292a-292c and capacitive elements 294a-294h configured to provide high-pass filtering to isolate the high-frequency component of the respective anode signal 206a-206d. Although embodiments are illustrated including various inductive and/or capacitive elements, it will be appreciated that any suitable elements can be used to passively split (i.e., diplex) the broadband (e.g. wideband) anode signals 206a-206d into a low-frequency narrowband signal 282a-282d and a high-frequency narrowband signal 284a-284d.

In some embodiments, the high-frequency components 282a-282d of each of the duplexing coupling circuits 280a-280d are combined (e.g., summed) to form a summed signal 232 for timing pick-off. The summed single 232 is provided to an analog timing pickoff circuit 240. As discussed above with respect to FIG. 2, the analog timing pickoff circuit 240 can include any suitable circuit elements for generating a timing pickoff signal 252a-252b.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A detector circuit, comprising:
a plurality of photomultiplier tubes each having an anode configured to generate an anode output signal; and
a frequency domain detector interface comprising a plurality of frequency domain coupling circuits, wherein each of the plurality of frequency domain coupling circuits is configured to receive the anode output signal from one of the plurality of photomultiplier tubes, wherein each of the plurality of frequency domain coupling circuits is configured to pickoff a first one of a high-frequency component and a low-frequency component from the anode output signal and generate a pass-through signal comprising a second one of the high-frequency component and the low-frequency component;
wherein each of the plurality of frequency domain coupling circuits comprises a high-frequency coupling circuit configured to pickoff the high-frequency component of the anode signal, and wherein the high-frequency coupling circuit comprises a radiofrequency directional coupler configured to pickoff the high-frequency component of the anode signal.

2. The detector circuit of claim 1, wherein each of the plurality of frequency domain coupling circuits comprises a low-frequency coupling circuit configured to pickoff the low-frequency component of the anode signal.

3. The detector circuit of claim 2, wherein the low frequency coupling circuit comprises a Balun transformer.

4. The detector circuit of claim 1, wherein the high-frequency coupling circuit comprises a transformer configured to pickoff the high-frequency component of the anode signal.

5. The detector circuit of claim 1, further comprising a summation timing circuits configured to receive the first one of the high-frequency component or the low-frequency component from each anode output signal and generate a summed timing signal by summing the received first one of the high-frequency component and the low-frequency component from each anode output signal.

6. The detector circuit of claim 5, wherein the summation timing circuit comprises a resistive-load summation timing circuit.

7. The detector circuit of claim 5, wherein the summation timing circuit comprises an inductive-load summation timing circuit.

8. The detector circuit of claim 5, wherein the summation timing circuit comprises a power combiner summation timing circuit.

9. The detector circuit of claim 5, wherein the summation timing circuit comprises a transformer-based summation timing circuit.

10. The detector circuit of claim 1, further comprising an analog frontend configured to receive the pass-through signal and generate a low-voltage differential signal, wherein the low-voltage differential signal is used for energy acquisition of anode output signal.

11. A detector circuit, comprising:
a plurality of photomultiplier tubes each having an anode configured to generate a broadband anode output signal; and
a frequency domain detector interface comprising a plurality of duplexing coupling circuits, wherein each of the plurality of duplexing coupling circuits is configured to receive the broadband anode output signal from one of the plurality of photomultiplier tubes and generate a narrowband low-frequency signal and a narrowband high-frequency signal,
wherein each of the duplexing coupling circuits comprises a low-frequency path and a high-frequency path, and wherein the low-frequency path comprises a first plurality of inductors and a first plurality of capacitors configured to provide low-pass filtering and the high-frequency path comprises a second plurality of inductors and a second plurality of capacitors configured to provide high-pass filtering.

12. The detector circuit of claim 11, further comprising an analog frontend configured to receive the narrowband low-frequency signal and generate a low-voltage differential signal, wherein the low-voltage differential signal is used for energy acquisition of anode output signal.

13. The detector circuit of claim 11, further comprising a summation timing circuit configured to receive the narrowband high-frequency signal from each of the plurality of duplexing coupling circuits and generate a summed high-frequency signal.

14. The detector circuit of claim 13, further comprising a timing pickoff circuit configured to receive the summed high-frequency signal and generate a timing pickoff signal.

15. The detector circuit of claim 13, wherein the summation timing circuit comprises a power combiner.

16. The detector circuit of claim 13, wherein the summation timing circuit comprises a transformer-based summation timing circuit.

17. A detector circuit, comprising:
- a plurality of photomultiplier tubes each having an anode configured to generate an anode output signal;
- a frequency domain detector interface comprising a plurality of coupling circuits, wherein each of the plurality of coupling circuits is configured to receive the anode output signal from one of the plurality of photomultiplier tubes and generate a low-frequency output signal and a high-frequency output signal;
- an analog frontend configured to receive the low-frequency output signal and generate one of a single-ended signal or a differential signal;
- a summation timing circuit configured to receive the high-frequency output signal and generate a summed high-frequency signal; and
- a timing pickoff circuit configured to receive the summed high-frequency signal and generate a timing pickoff signal.

* * * * *